United States Patent
Liu

(10) Patent No.: US 8,633,980 B2
(45) Date of Patent: Jan. 21, 2014

(54) MONITORING APPARATUS HAVING A DETACHABLE DISPLAY AND A POWER FAILURE PROTECTION

(76) Inventor: Da-Ming Liu, New Taipei (TW)

(*) Notice: Subject to any disclaimer, the term of this patent is extended or adjusted under 35 U.S.C. 154(b) by 369 days.

(21) Appl. No.: 13/051,004

(22) Filed: Mar. 18, 2011

(65) Prior Publication Data

US 2012/0236138 A1  Sep. 20, 2012

(51) Int. Cl.
*H04N 7/18* (2006.01)

(52) U.S. Cl.
USPC ........................................ 348/84; 348/E7.085

(58) Field of Classification Search
USPC ................. 348/55, 135, 373, 82, 84; 382/103
See application file for complete search history.

(56) References Cited

U.S. PATENT DOCUMENTS

| | | | | |
|---|---|---|---|---|
| 5,879,289 A * | 3/1999 | Yarush et al. | ................ | 600/179 |
| 6,091,453 A * | 7/2000 | Coan et al. | .................... | 348/373 |
| D560,804 S * | 1/2008 | Pease et al. | .................. | D24/138 |
| 7,431,619 B2 * | 10/2008 | Boehnlein et al. | ............ | 439/882 |
| D594,361 S * | 6/2009 | Miller et al. | .................... | D10/78 |
| D594,362 S * | 6/2009 | Miller | ............................ | D10/78 |
| 7,584,534 B2 * | 9/2009 | Pease et al. | ...................... | 29/729 |
| 7,758,495 B2 * | 7/2010 | Pease et al. | .................. | 600/104 |
| 2006/0038499 A1 * | 2/2006 | Yeh | ................................ | 315/149 |
| 2006/0158549 A1 * | 7/2006 | Digweed et al. | .............. | 348/373 |
| 2009/0198990 A1 * | 8/2009 | Watt et al. | ......................... | 713/2 |
| 2009/0229842 A1 * | 9/2009 | Gray et al. | ...................... | 173/20 |
| 2010/0033563 A1 * | 2/2010 | Boehnlein et al. | ............. | 348/84 |
| 2010/0277578 A1 * | 11/2010 | Mitchell | ......................... | 348/61 |
| 2011/0018992 A1 * | 1/2011 | Liu | ................................ | 348/135 |
| 2011/0169940 A1 * | 7/2011 | Babb | .............................. | 348/84 |
| 2011/0228076 A1 * | 9/2011 | Liu | ................................ | 348/84 |

* cited by examiner

*Primary Examiner* — Christopher S Kelley
*Assistant Examiner* — Ana Picon-Feliciano
(74) *Attorney, Agent, or Firm* — Bacon & Thomas, PLLC

(57) ABSTRACT

The present invention discloses a monitoring apparatus having a detachable display device and a power failure protection, wherein the monitoring apparatus comprises a main body and the display device. When the display device is installed to the main body, a second terminal socket of the display device and a first terminal socket of the main body are inlaid, such that corresponding connecting terminals exposed out of the main body and display device can be electrically conducted with each other. When the display device is detached from the main body, a second switch of the display device and a first switch of the main body are in an opened status respectively, such that the connecting terminals exposed out of the main body and display device cannot receive electric power, however, the main body and display device can still be electrically coupled by a transmission line through corresponding ports thereof.

4 Claims, 3 Drawing Sheets

MONITORING APPARATUS HAVING A DETACHABLE DISPLAY AND A POWER FAILURE PROTECTION

FIELD OF THE INVENTION

The present invention relates to a monitoring apparatus, more particularly to a monitoring apparatus comprising a main body and a display device, wherein the display device can be installed to or detached from the main body and, when the display device is detached from the main body, corresponding terminals exposed out of the main body and the display device for electrically connecting the display device and the main body will not receive electric power from a battery of the main body.

BACKGROUND OF THE INVENTION

As industrial technologies advance, various types of approachable tools available in the market are provided for general users or maintenance technicians to inspect conditions of environments or constructions conveniently. For example, the maintenance technicians generally inspect the internal condition of a pipeline such as a water pipe or a gas pipe buried inside a wall or under the ground of most residences by using a tool (such as a steel chisel, an electric hammer, and an electric drill) to dig through the wall or the ground, and extending a monitoring apparatus into the problemed pipeline to inspect the condition of the pipeline, once the pipeline is broken, damaged or clogged.

With reference to FIG. 1 for the structure of a conventional monitoring apparatus, the monitoring apparatus comprises a main body 10, a serpent tube 11, a camera module 12 and a display device 13, wherein an end of the serpent tube 11 is coupled to the main body 10, and the serpent tube 11 is flexible and deformable to meet user requirements or to fit the shape of a pipe to be repaired, and another end of the serpent tube 11 is coupled to the camera module 12. The main body 10 includes a first terminal socket 101, a first port 103, and a built-in power supply (not shown in the figure), and the first terminal socket 101 includes a plurality of first connecting terminals 1011 coupled to the first port 103 respectively through the serpent tube 11 and electrically coupled to the camera module 12 for receiving a video signal transmitted from the camera module 12 and supplying electric power to the camera module 12. In addition, the display device 13 includes a second terminal socket 131 and a second port 133, the second terminal socket 131 includes a plurality of second connecting terminals 1311, the second connecting terminals 1311 and second port 133 are electrically coupled to a control circuit board of the display device 13 respectively, and the display device 13 can be installed directly to the main body 10 and electrically coupled to the main body 10 through connecting the connecting terminals 1011, 1311 in the terminal sockets 101, 131, or through inserting plugs at both ends of a transmission line into the ports 103, 133 respectively.

In FIG. 1, if a user wants to maintain or repair a pipeline by using the monitoring apparatus, the user simply digs through the wall or the ground, and then drills an opening from the exposed pipe, and holds the main body 10 to extend the camera module 12 and the serpent tube 11 into the pipeline through the opening, such that the main body 10 can receive video data of images captured by the camera module 12 and transmit the video data to the display device 13 through the terminal sockets 101, 131 or the ports 103, 133, so as to allow users to view the video data of the images captured by the camera module 12 from the display device 13 and know about the conditions inside the pipeline to troubleshoot the cause of the pipeline failure. With the aforementioned monitoring apparatus, the users simply need to dig through the wall or ground once or twice to confirm the exact position of the failed pipeline for the repair, so as to avoid digging through the wall or ground for too many times and further reduce the time and material cost required for the repair work. In the meantime, a transmission line is applied, so that the monitoring apparatus 1 allows a user to hold the main body 10 to adjust the angle of bending the serpent tube 11 freely and allows another user to hold the display device 13 to view the condition inside the pipeline to make necessary records or analyses.

However, the design of the conventional monitoring apparatus still has drawbacks. In FIG. 1, when the main body 10 of the monitoring apparatus 1 is installed to the display device 13, the first connecting terminals 1011 are electrically coupled to the corresponding second connecting terminal 1311, such that a power supply of the main body 10 can supply a current to the second connecting terminals 1311 through the first connecting terminals 1011 in order to supply electric power for the operation of the display device 13. After a user turns on the display device 13, the control circuit board will transmit the received current to the corresponding first connecting terminals 1011 through the second connecting terminals 1311 to turn on the camera module 12. In other words, the camera module 12 starts its operation only if the display device 13 is powered on. When the main body 10 of the monitoring apparatus 1 is installed to the display device 13 through a connecting wire, and the power supply of the main body 10 supplies the current to the display device 13 through the transmission line, and the electric power is then supplied from the display device 13 to the camera module 12. In the meantime, since the power supply of the main body 10 is not coupled to the first connecting terminal 1011, and the control circuit board of the display device 13 is not coupled to the second connecting terminal 1311, therefore the connecting terminals 1011, 1311 still can transmit the current received from the power supply. If any foreign substance (such as metal debris) falls into the terminal sockets 101, 131 and across the adjacent first connecting terminal 1011 or second connecting terminal 1311, abnormal operations of monitoring apparatus 1 may occur due to short circuits of the adjacent connecting terminals 1011, 1311. Even worse, a fire may occur and jeopardize the safety of users due to sparks produced by the short circuits.

In view of the description above, the conventional monitoring apparatus does not come with any safety design for protecting a possible short circuit of the connecting terminal or avoiding the inconvenience and danger of using the conventional monitoring apparatus. Therefore, it is an important subject for the present invention to overcome the shortcomings of the conventional monitoring apparatus by improving the safety of the monitoring apparatus.

SUMMARY OF THE INVENTION

In view of the aforementioned shortcomings of the conventional monitoring apparatus with a circuit design that may cause a short circuit or even a fire accident, the inventor of the present invention based on years of experience in the related industry to conduct extensive researches and experiments, and finally designed and developed a monitoring apparatus having a detachable display device and a power failure protection for overcoming the shortcomings of the prior art.

Therefore, it is a primary objective of the present invention to provide a monitoring apparatus having a detachable display device and a power failure protection, wherein the monitoring apparatus comprises a display device that can be detached from a main body thereof and can still be electrically coupled to the main body simply by a transmission line and, at this circumstance, connecting terminals exposed outside the main body and display device cannot transmit electric power provided by the monitoring apparatus, such that the adjacent connecting terminals will not have any short circuit problem caused by the adhesion of foreign substances, and the safety of using the monitoring apparatus can be improved greatly. The monitoring apparatus comprises a camera module, a serpent tube, the main body and the display device, wherein the serpent tube is coupled to the camera module and the main body. The main body comprises a first terminal socket, a first port and a plurality of first switches disposed at the top of the main body, and a battery and a first circuit disposed inside the main body. The first terminal socket includes a plurality of main body connecting terminals, wherein one of the main body connecting terminals is electrically coupled to the battery through the first circuit and the serpent tube, and the remaining main body connecting terminal is electrically coupled to the camera module through the first circuit and the serpent tube. The first port is electrically coupled to the camera module through the first circuit and the serpent tube, and provided for connecting to a first plug of a transmission line. The first switches are coupled to some of the main body connecting terminals for disconnecting or connecting the power supplied to the corresponding main body connecting terminals. In addition, the display device has a screen disposed at the top of the display device, a second terminal socket, a second port and a plurality of second switches disposed at the bottom of the display device, and a control circuit board and a second circuit disposed in the display device. The second terminal socket includes a plurality of display terminals electrically coupled to the control circuit board, and the second port is electrically coupled to the control circuit board through the second circuit and provided for connecting to a second plug of the transmission line, and the second switches are coupled to some of the display terminals respectively for disconnecting or connecting the power supplied to the corresponding display terminal. When the display device is installed to the main body, the second terminal socket and the first terminal socket are inlaid, such that the corresponding main body connecting terminals and display terminals can be electrically conducted with each other, and the corresponding first and second switches are in a closed status respectively. When the display device is not installed to the main body, the corresponding first and second switches are in an opened status respectively, such that the corresponding main body connecting terminals and display terminals are disconnected from each other and fail to receive electric power from the battery. Through the first and second plugs of the transmission line, the first and second ports can be electrically coupled to each other, so that the control circuit can be electrically conducted with the battery and the camera module.

DETAILED DESCRIPTION OF THE PREFERRED EMBODIMENTS

In view of the poor circuit design of the conventional monitoring apparatus with the hidden worries of short circuits and fire accidents, the inventor of the present invention based on years of experience in the related industry to conduct extensive researches and experiments, and developed a monitoring apparatus in accordance with the present invention capable of disconnecting power supplied to connecting terminals of the monitoring apparatus if the connecting terminals are exposed outside the monitoring apparatus, so as to overcome the shortcomings of the prior art.

Figure 1:
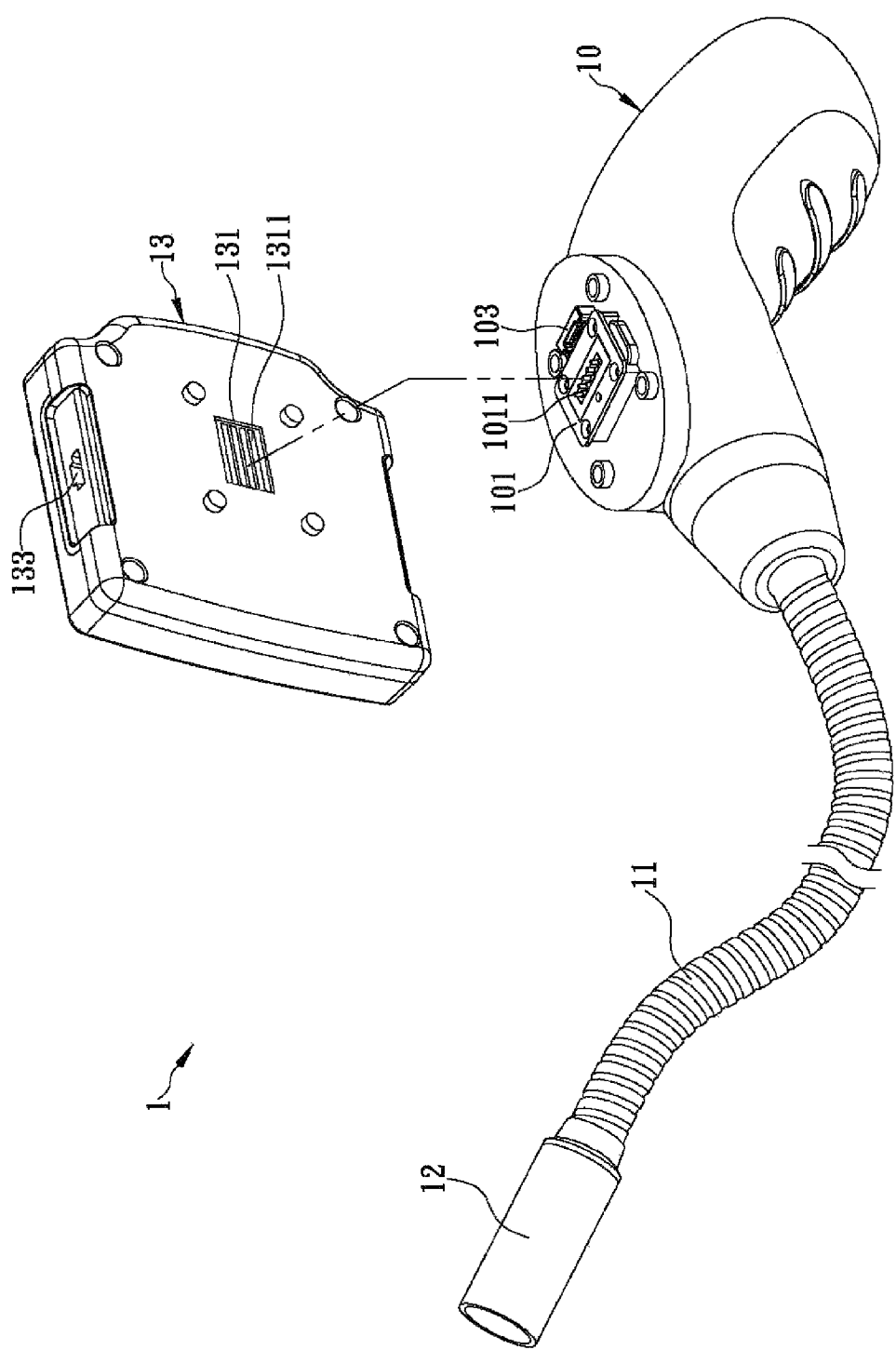
FIG. 1 is a schematic view of a conventional monitoring apparatus.
Figure 2:
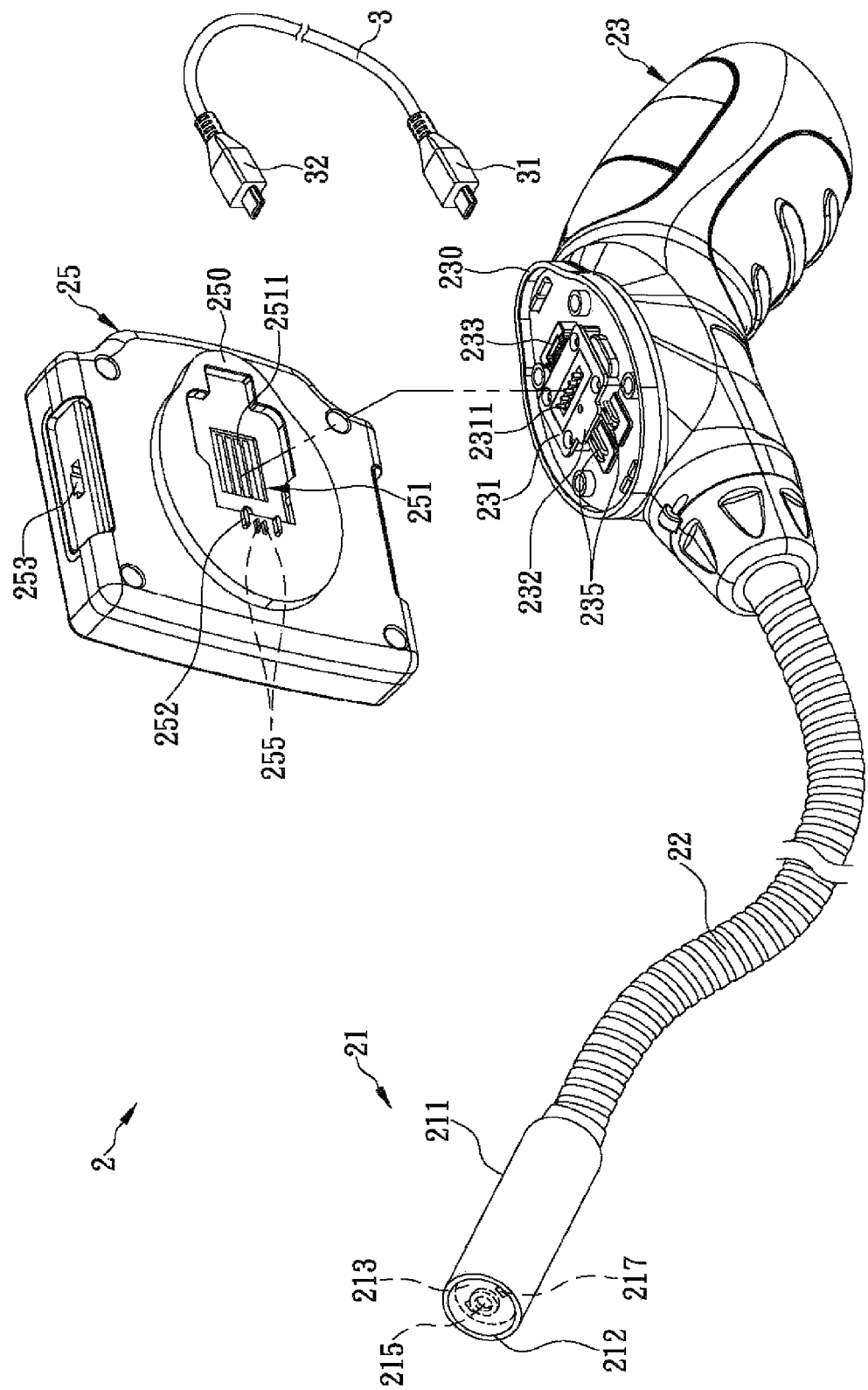
FIG. 2 is a schematic view of a monitoring apparatus of the present invention.

With reference to FIG. 2 for a monitoring apparatus having a detachable display device and a power failure protection in accordance with a preferred embodiment of the present invention, the monitoring apparatus 2 comprises a camera module 21, a serpent tube 22, a main body 23 and a display device 25, wherein the camera module 21 includes a sleeve 211 and a circuit board 213, a lens 212 is installed at an end of the sleeve 211, the circuit board 213 is installed in the sleeve 211, and a camera lens 215 and a light emitting element 217 (such as a light emitting diode) are installed on the circuit board 213 at positions corresponding to the lens 212. Further, both ends of the serpent tube 22 are coupled to the camera module 21 and the main body 23 respectively, and the serpent tube 22 can be bent into different angles, and the main body 23 has a first inlaying area 230 disposed at the top of the main body 23, and the display device 25 has a second inlaying area 250 disposed at the bottom of the display device 25, wherein the first inlaying area 230 and the second inlaying area 250 are of the same shape, such that the display device 25 can be installed to the main body 23.

Figure 3:
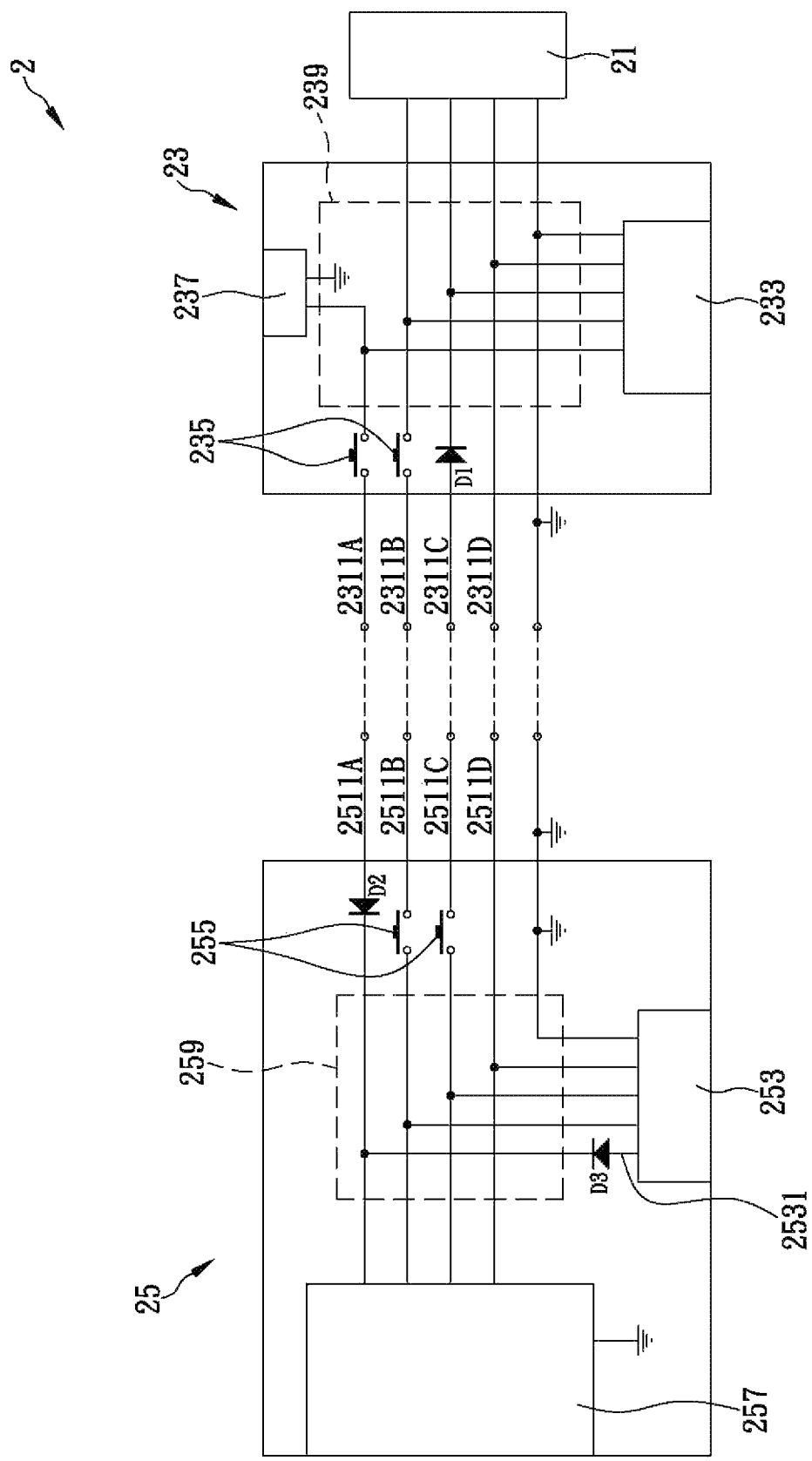
FIG. 3 is a schematic circuit diagram of a monitoring apparatus of the present invention.

In FIGS. 2 and 3, the main body 23 includes a first terminal socket 231, a first port 233 and a plurality of first switches 235, and a battery 237 and a first circuit 239 installed in the main body 23, and the first terminal socket 231 has a plurality of main body connecting terminals 2311. For the purpose of simplifying the description of the connection relation of the following circuits, the main body connecting terminals 2311 are divided into a first main body connecting terminal 2311A, a second main body connecting terminal 2311B, a third main body connecting terminal 2311C and a fourth main body connecting terminal 2311D. The first main body connecting terminal 2311A is electrically coupled to the battery 237 through the first circuit 239, and the second main body connecting terminal 2311B is passed through the serpent tube 22 and electrically coupled to the camera lens 215 through the first circuit 239, and the third main body connecting terminal 2311C is passed through the serpent tube 22 and electrically coupled to the light emitting element 217 through the first circuit 239, and the fourth main body connecting terminal 2311D is passed through the serpent tube 22 and electrically coupled to the camera module 21 through the first circuit 239 for receiving a video signal transmitted from the camera module 21, wherein one of the first switches 235 is coupled between the first main body connecting terminal 2311A and the first circuit 239, and another first switch 235 is coupled between the second main body connecting terminal 2311B and the first circuit 239, such that, when the first switches 235 are in a closed status respectively, the first main body connecting terminal 2311A and the second main body connecting terminal 2311B can be electrically coupled to the first circuit 239 or, when the first switches 235 are in an opened status respectively, the first main body connecting terminal 2311A and the second main body connecting terminal 2311B are electrically disconnected with the first circuit 239. In the preferred embodiment as shown in FIG. 2, the first switches 235 are elastic metal plates that can be pressed to define the closed status and released to define the opened status respectively.

In FIGS. 2 and 3, a first diode D1 is installed between the third main body connecting terminal 2311C and the first circuit 239, wherein an anode of the first diode D1 is coupled to the third main body connecting terminal 2311C, and a cathode of the first diode D1 is coupled to the first circuit 239, such that the current can only be transmitted from the third main body connecting terminal 2311C to the first circuit 239, but cannot be transmitted in a reverse direction from the first circuit 239 to the third main body connecting terminal 2311C. In addition, the first port 233 can be electrically coupled to the battery 237 through the first circuit 239, electrically coupled to the camera module 21 through the first circuit 239 and the serpent tube 22, and connected to a first plug 31 of a transmission line 3 for transmitting a current of the battery 237 to the transmission line 3, or receiving the current and video signal transmitted from the transmission line 3.

In FIGS. 2 and 3, the display device 25 includes a second terminal socket 251, a second port 253 and a plurality of second switches 255, and a control circuit board 257 and a second circuit 259 installed in the display device 25, and the second terminal socket 251 includes a plurality of display terminals 2511. Similarly, for the purpose of simplifying the description of the connection relation of the following circuits, the display terminals 2511 are divided into a first display terminal 2511A, a second display terminal 2511B, a third display terminal 2511C and a fourth display terminal 2511D. The display terminals 2511A, 2511B, 2511C, 2511D are electrically coupled to the control circuit board 257 through the second circuit 259 for transmitting a current or a video signal to the control circuit board 257 or receiving a current transmitted from the control circuit board 257. In addition, one of the second switches 255 is coupled between the second display terminal 2511B and the second circuit 259, and another second switch 255 is coupled between the third display terminal 2511C and the second circuit 259, such that, when the second switches 255 are in a closed status respectively, the second display terminal 2511B and the third display terminal 2511C are electrically coupled to the second circuit 259 or, when the second switches 255 are in an opened status respectively, the second display terminal 2511B and the third display terminal 2511C are electrically disconnected from the second circuit 259. In the preferred embodiment as shown in FIG. 2, the second switches 255 are elastic metal places that can be pressed to define the closed status and released to define the opened status.

In FIGS. 2 and 3, a second diode D2 is further installed between the first display terminal 2511A and the second circuit 259, wherein an anode of the second diode D2 is coupled to the first display terminal 2511A and a cathode of second diode D2 is coupled to the second circuit 259, such that the current can only be transmitted from the first display terminal 2511A to the second circuit 259, but cannot be transmitted in a reverse direction from the second circuit 259 to the first display terminal 2511A. In addition, the second port 253 is electrically coupled to the control circuit board 257 through the second circuit 259, and can be connected to a second plug 32 of the transmission line 3 for receiving a current transmitted from the transmission line 3 or transmitting a current and a video signal to the transmission line. In addition, a battery transmission circuit 2531 of the second port 253 is electrically coupled to the battery 237 of the main body 23 through the transmission line 3, and a third diode D3 is installed between the battery transmission circuit 2531 and the second circuit 259, wherein an anode of the third diode D3 is coupled to the battery transmission circuit 2531, and a cathode of the third diode D3 is coupled to the second circuit 259, such that the current can only be transmitted from the battery transmission circuit 2531 to the second circuit 259, but cannot be transmitted in a reverse direction from the second circuit 259 to the battery transmission circuit 2531.

In FIGS. 2 and 3, the main body 23 includes a first trigger 232, and the display device 25 includes a second trigger 252, wherein the first trigger 232 of this preferred embodiment is a plate integrally formed with the first terminal socket 231a, and the second trigger 252 of this preferred embodiment is comprised of two protruding pillars, such that when the display device 25 is installed to the main body 23, the second terminal socket 251 can be inlaid with the first terminal socket 231, and the second trigger 252 will press against the first switch 235 to define a closed status of the first switch 235, and the first trigger 232 will press against the second switch 255 to define a closed status of the second switch 255. In the meantime, the first main body connecting terminal 2311A will be coupled to the first display terminal 2511A, the second main body connecting terminal 2311B will be coupled to the second display terminal 2511B, the third main body connecting terminal 2311C will be coupled to the third display terminal 2511C, and the fourth main body connecting terminal 2311D will be coupled to the fourth display terminal 2511D, such that after a user turns on the display device 25, the current of the battery 237 can be transmitted sequentially through the first circuit 239, the first main body connecting terminal 2311A, the first display terminal 2511A, the second diode D2 and the second circuit 259 to the control circuit board 257, and the control circuit board 257 can transmit the current of the battery 237 through the second circuit 259 to the second display terminal 2511B and the third display terminal 2511C, such that the second display terminal 2511B can transmit the current sequentially through the second main body connecting terminal 2311B, the first circuit 239 and the serpent tube 22 to the camera lens 215 of the camera module 21 to drive the operation of the camera lens 215, and the third display terminal 2511C can transmit the current sequentially through the third main body connecting terminal 2311C, the first diode D1, the first circuit 239 and the serpent tube 22 to the light emitting element 217 of the camera module 21 to drive the light emitting element 217 to emit light, and the camera lens 215 can capture a frame at a dark place, and the circuit board 213 can convert the captured frame into a video signal, and transmit the video signal sequentially through the serpent tube 22, the first circuit 239, the fourth main body connecting terminal 2311D, the fourth display terminal 2511D and the second circuit 259 to the control circuit board 257, such that the control circuit board 257 can display a frame included in the video signal onto a screen of the display device 25 and allow a user to view the content of the frame. Due to the way of installing the third diode D3, the current transmitted from the first display transmitting terminal 2511A cannot be transmitted to the second port 253 through the battery transmission circuit 2531.

In FIGS. 2 and 3, if the display device 25 is not installed to the main body 23, the triggers 232, 252 will not be able to press against the corresponding switches 255, 235, such that the corresponding first switch 235 and second switch 255 are in an opened status respectively. At this moment, the display device 25 can be electrically coupled to the first port 233 and the second port 253 through the first plug 31 and the second plug 32 of the transmission line 3. Therefore, the current of the battery 237 will be transmitted through the first port 233, the transmission line 3, the second port 253, the battery transmission circuit 2531 and the second circuit 259 to the control circuit board 257, and then the control circuit board 257 will transmit the current through the second circuit 259, the second port 253, the transmission line 3, the first port 233, the first circuit 239 and the serpent tube 22 to the camera module 21 to drive the camera lens 215 and the light emitting element 217 and receive the video signal returned from the camera module 21. Due to the installation of the first switches 235 and the first diode D1, the current of the battery 237 and current received from the first port 233 cannot be transmitted to the first main body connecting terminal 2311A, the second main body connecting terminal 2311B and the third main body connecting terminal 2311C respectively. Due to the installation of the second switches 255 and the second diode D2, the current received from the second port 253 and current transmitted from the control circuit board 257 cannot be transmitted to the first display terminal 2511A, the second display terminal 2511B and the third display terminal 2511C, so that the adjacent connecting terminals 2311, 2511 will not have short circuit problems caused by the attachment of foreign substances, and the safety of the monitoring apparatus 2 can be improved significantly.

It is noteworthy to point out that the second port 253 is disposed on a lateral side of the display device 25 and exposed outside the display device 25 in accordance with the foregoing preferred embodiment as shown in FIGS. 2 and 3, so that the installation of the third diode D3 is required. However, the manufacturers can change the position of installing the second port 253, such that when the main body 23 and the display device 25 are installed, the second port 253 can be covered to prevent foreign substances from accumulating in the second port 253. Alternatively, the manufacturers may not install any third diode D3. In addition, the manufacturers can use a switch to substitute the diode of the aforementioned preferred embodiment to achieve the same effect of disconnecting or connecting the current.

While the invention has been described by way of example and in terms of a preferred embodiment, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements and procedures.

What is claimed is:

1. A monitoring apparatus having a detachable display device and a power failure protection, comprising:
a camera module comprising a sleeve having a lens installed at an end of the sleeve, and a circuit board accommodated in the sleeve and having a camera lens and a light emitting element installed at positions corresponding to the lens;
a serpent tube, with an end coupled to the camera module;
a main body, coupled to another end of the serpent tube, and including a first terminal socket, a first port and a plurality of first switches disposed on a top of the main body, and a battery and a first circuit disposed in the main body, wherein the first terminal socket has a plurality of main body connecting terminals, the main body connecting terminals comprise a first main body connecting terminal electrically coupled to the first circuit through one of the first switches for receiving current transmitted from the battery through the first circuit, a second main body connecting terminal electrically coupled to the first circuit through another first switch for transmitting the current to the camera lens through the first circuit, a third main body connecting terminal electrically coupled to the first circuit through a first diode for transmitting the current to the light emitting element through the first circuit, and a fourth main body connecting terminal for receiving a video signal transmitted from the camera module through the first circuit; wherein an anode of the first diode is coupled to the third main body connecting terminal, and a cathode of the first diode is coupled to the first circuit; wherein one of the main body connecting terminals is electrically coupled to the battery through the first circuit, the remaining main body connecting terminals pass through the serpent tube and are electrically coupled to the camera module through the first circuit, the first port passes through the serpent tube and is electrically coupled to the camera module through the first circuit for connecting to a first plug of a transmission line, the first switches are coupled to a portion of main body connecting terminals respectively for disconnecting or connecting corresponding power supply currents of the main body connecting terminals respectively, and the camera module and the circuit board receive the current transmitted from the first circuit and transmit a video signal to the first circuit through the serpent tube; and a display device, having a second terminal socket, a second port and a plurality of second switches, a control circuit board and a second circuit installed in the display device, wherein the second terminal socket has a plurality of display terminals electrically connectable to the control circuit board, the second port is electrically coupled to the control circuit board through the second circuit and provided for connecting to a second plug of the transmission line, and the second switches are respectively and electrically coupled to a portion of the display terminals for disconnecting or connecting the power supply current of the display terminal; wherein the display terminal comprises a first display terminal electrically coupled to the second circuit through a second diode and transmitting current to the control circuit board through the second circuit, a second display terminal electrically coupled to the second circuit through one of the second switches and receiving a current transmitted from the control circuit board through the second circuit, a third display terminal electrically coupled to the second circuit through another second switch for receiving a current transmitted from the control circuit board through the second circuit, and a fourth display terminal for transmitting a video signal to the control circuit board through the second circuit; wherein, when the first terminal socket and the second terminal socket are inlaid with each other, the first display terminal is electrically coupled to the first main body connecting terminal, an anode of the second diode is coupled to the first display terminal, and a cathode of the second diode is coupled to the second circuit; when the first terminal socket and the second terminal socket are inlaid with each other, the second display terminal is electrically coupled to the second main body connecting terminal; when the first terminal socket and the second terminal socket are inlaid with each other, the third display terminal is electrically coupled to the third main body connecting terminal; and when the first terminal socket and the second terminal socket are inlaid with each other, the fourth display terminal is electrically coupled to the fourth main body connecting terminal;

thereby, when the display device is installed to the main body, the second terminal socket is inlaid with the first terminal socket, such that the corresponding main body connecting terminal and display terminal are electrically conducted and the first switch and the second switch are in a closed status respectively and, when the display device is detached from the main body, the first switch and the second switch are in an opened status respectively, the main body connecting terminal and display terminal cannot receive electric power from the battery, and when the second port of the display device is electrically coupled to the first port of the main body via the first plug and the second plug of the transmission line, the control circuit is electrically conducted with the battery and the camera module.

2. The monitoring apparatus of claim 1, further comprising a third diode, wherein an anode of the third diode is coupled to a battery transmission circuit of the second port, and a cathode of the third diode is coupled to the second circuit.

3. The monitoring apparatus of claim 1, wherein the main body includes a first trigger, and the display device includes a second trigger, wherein, when the first terminal socket and the second terminal socket are inlaid with each other, the first trigger presses against the second switches to define a closed status respectively, and the second trigger presses against the first switches to define an opened status respectively.

4. The monitoring apparatus of claim 2, wherein the main body includes a first trigger, and the display device includes a second trigger, wherein, when the first terminal socket and the second terminal socket are inlaid with each other, the first trigger presses against the second switches to define a closed status respectively, and the second trigger presses against the first switches to define an opened status respectively.

* * * * *